(12) United States Patent
Massaro et al.

(10) Patent No.: US 6,924,256 B2
(45) Date of Patent: Aug. 2, 2005

(54) LIQUID CLEANSING COMPOSITION HAVING SIMULTANEOUS EXFOLIATING AND MOISTURIZING PROPERTIES

(75) Inventors: Michael Massaro, Monroe, CT (US); Jessica Weiss Goldberg, Fairfield, CT (US); Krishna Kumar Subramanyan, Danbury, CT (US); Anthony William Johnson, Fairfield, CT (US); Craig Stephen Slavtcheff, Guilford, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 431 days.

(21) Appl. No.: 10/290,609

(22) Filed: Nov. 8, 2002

(65) Prior Publication Data

US 2004/0091446 A1 May 13, 2004

(51) Int. Cl.$^7$ ............................................... A61K 7/075
(52) U.S. Cl. ..................... 510/119; 424/70.19; 510/129
(58) Field of Search ................................. 510/119, 130, 510/417; 424/70.1, 70.21

(56) References Cited

U.S. PATENT DOCUMENTS

| | | |
|---|---|---|
| 3,723,325 A | 3/1973 | Parran Jr. |
| 4,557,853 A | 12/1985 | Collins |
| 4,565,647 A | 1/1986 | Llenado |
| 4,992,476 A | 2/1991 | Geria |
| 5,009,814 A | 4/1991 | Kelkenberg |
| 5,147,576 A | 9/1992 | Montague |
| 5,389,279 A | 2/1995 | Au et al. |
| 5,393,466 A | 2/1995 | Ilardi et al. |
| 5,658,577 A | 8/1997 | Fowler et al. |
| 5,753,245 A | 5/1998 | Fowler et al. |
| 5,952,286 A * | 9/1999 | Puvvada et al. ............ 510/417 |
| 5,958,856 A * | 9/1999 | Yianakopoulos et al. ... 510/236 |
| 6,063,366 A | 5/2000 | Sugai et al. |

FOREIGN PATENT DOCUMENTS

| | | |
|---|---|---|
| EP | 0 295 885 | 1/1992 |
| EP | 0571193 * | 5/1993 ............ A61K/7/48 |
| EP | 0 571 193 | 9/1999 |
| GB | 1 579 934 | 11/1980 |
| GB | 2 259 519 | 3/1993 |
| WO | 01/19949 | 3/2001 |

OTHER PUBLICATIONS

International Search Report No. PCT/EP 03/11812 dated Feb. 23, 2004, 3 pp.

\* cited by examiner

*Primary Examiner*—Thurman K. Page
*Assistant Examiner*—David L. Vanik
(74) *Attorney, Agent, or Firm*—Alan A. Bornstein

(57) ABSTRACT

Liquid lamellar cleansing compositions are described that contain synthetic surfactants, hydrophilic emollients and exfoliant particles where 80% or more of the particles have a major axis length of between 100 and 1000 microns. The combination of the mild surfactants, moisturizers, and exfoliants provide the user with simultaneous moisturization and exfoliation in a convenient liquid cleansing product.

18 Claims, No Drawings

LIQUID CLEANSING COMPOSITION HAVING SIMULTANEOUS EXFOLIATING AND MOISTURIZING PROPERTIES

BACKGROUND OF THE INVENTION

1. Field of the Invention

The present invention relates to a liquid cleansing composition suitable for topical application for cleansing the human body, such as the skin and hair. In particular, it relates to a lamellar structured liquid cleansing composition that is mild to the skin and which also exfoliates the skin.

2. The Related Art

Exfoliating liquid cleansing compositions are well known. However, the majority of them are not moisturizing. In addition the majority of them are not gentle enough for daily use while still providing the sensation and utility required of exfoliating particles.

Certain prior art liquid cleansing compositions with exfoliants have been described. U.S. Pat. No. 5,658,577 to Fowler et al., issued on Aug. 19, 1997 discloses an non-lamellar isotropic gel cleansing composition with very small exfoliant particles under 75 microns that are not perceptable to the user and that contains up to 20% of an hydrophobic emollient. U.S. Pat. No. 5,732,245 to Fowler et al., issued on May 19, 1998 discloses an non-lamellar isotropic liquid cleansing composition with very small exfoliant particles under 75 microns that are not perceptable to the user and that contains up to 50% of an hydrophobic emollient.

Surprisingly it has been found that mild liquid cleansing compositions having one or more syndet surfactants, one or more hydrophobic emollients at a level in excess of 10%, and exfoliants of a specific particle size range provide the user with enhanced moisturization and exfoliation simultaneously. This causes the user's exfoliated skin to appear fresh and healthy as it removes the dull layer of dead skin, accompanied with deep cleansing leading to less clogged pores while at the same time moisturizing the skin to minimize irritation and dryness as shown by various art recongnized techniques described below.

While not wishing to be bound by the following skin treatment theories, Applicants believe that exfoliation improves skin cleansing by helping to mechanically remove dirt and oil from the skin. Exfoliation also is believed to aid the process of desquamation. Desquamation is a natural process by which corneocytes are removed from the stratum corneum, which is the top layer of skin cells. Corneocytes are simply the cells that comprise the stratum corneum, and they are constantly being removed as the skin regenerates. Exfoliation aids in removing the flaky corneocytes that are ready to detach from the stratum corneum, and so promotes smoother, less flaky skin.

Other potential health benefits to exfoliation in addition to improved scale (flake) removal and oil removal, as suggested above, are reduction in bacteria on the skin, and increased blood flow to the skin due to the mechanical stimulation.

The inventive liquid cleansing composition under actual use conditions is expected to show improvements in skin softness, skin smoothness, and similar consumer perceived benefits such as exfoliation efficiency, mildness, moisturization efficiency, deposition efficiency, cleansing efficiency, and a liquid cleansing composition property such as skin abrasiveness, etc. based on changes from the baseline for these measurements using liquid cleansing compositions without the inventive composition as quantified using the test methods described below.

Applicants have discovered that a stable exfoliating liquid cleansing product can be prepared having a lamellar phase preferably having a viscosity in the range of about 80,000 cps to 300,000, more preferably about 50,000 to 150,000 (T-bar) at 25° C. Preferably the viscosity has an upper limit of 300,000 cps at 25° C. The lamellar phase and exfoliating particles preferably have different colors or other visual differences.

SUMMARY OF THE INVENTION

In one aspect of the invention is a lamellar liquid cleansing composition, comprising:
  a. about 1 to 65% by wt. of one or more anionic surfactants;
  b. about 0.1 to 25% by wt. of one or more amphoteric surfactants;
  c. at least about 10% by wt. of total surfactants including one or more of anionic, amphoteric, nonionic surfactants, or a blend thereof;
  d. an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin;
  e. about 7 to about 40% by wt. of the total composition of a lipophilic emollient; and
  f. an effective amount of exfoliant particles for exfoliating the skin during cleansing wherein at least about 80% by wt. of the particles have a particle size dimension along the major axis of the particle of from about 100 microns to about 1000 microns; and In another aspect of the invention is a method for simultaneously exfoliating and moisturizing the skin comprising the steps of:
  a) providing a cleansing composition including
    i) about 1 to 65% by wt. of one or more anionic surfactants;
    ii) about 0.1 to 25% by wt. of one or more amphoteric surfactants;
    iii) an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin;
    iv) about 7 to 40% by wt. of the total composition of a lipophilic emollient;
    v) an effective amount of exfoliant particles for exfoliating the skin during cleansing wherein at least about 80% by wt. of the particles have a particle size dimension along the major axis of the particle of from about 100 microns to about 1000 microns.
  b) applying the composition to the skin;
  c) adding sufficient water to wet the skin and develop a lather;
  d) rubbing the lather onto the skin for a time sufficient to remove dead skin cells and coat the underlying skin with the hydrophilic emollient.

DETAILED DESCRIPTION OF THE INVENTION

In one aspect of the present invention is a liquid cleansing composition, having:
- a. about 1 to 65% by wt., preferably 5 to 25% by wt. of one or more anionic surfactants;
- b. about 0.1 to 25% by wt., preferably 1 to 8% by wt. of one or more amphoteric surfactants;
- c. at least about 10% by wt. of total surfactants including one or more of anionic, amphoteric, nonionic surfactants, or a blend thereof;
- d. an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin. Preferably the lamellar phase inducing structurant is present at about 0.1% to about 15% by wt., more preferably 0.5 to 5% by wt. of the total composition.
- e. about 7 to about 40%, preferably 15–30% by wt. of the total composition of a lipophilic emollient. More preferably the total lipophilic emollient is in a concentration greater than about 10%, most preferably 12%; and
- f. an effective amount of exfoliant particles for exfoliating the skin during cleansing wherein at least about 80% by wt. of the particles have a particle size dimension along the major axis of the particle of from about 100 microns to about 1000 microns; and Advantageously, the composition removes at least about 50%, preferably at least 80% of surface dead skin cells according to the d-squame comparison test defined below and simultaneously will provide a minimum deposition of about 5 micrograms, preferably more than about 10 micrograms per square centimeter of a lipophilic emollient. Preferarably the ratio of total anionic surfactants to total amphoteric surfactants is in the range of about 5 to 1, preferably 2.5 to 1.

More preferably, the composition provides measurable exfoliation according to the d-squame test comparison without inducing skin damage of more than a 10% change in degree of skin whiteness or more than a 10% change in degree of skin redness as determined by a cross polarized skin imaging test comparison after 3 washing applications per day for one day as defined below.

Advantageously, the inventive cleansing composition further includes about 1 to 10% by wt., preferably 3 to 8% by wt. of the total composition of humectants. Preferably the humectants are selected from glycerin and derivatives, propylene glycol and derivatives, saccaharides and polysaccharides such as maltodextrin, sorbitol, honey, and the like; allantoin, betaine, lactic acid, sodium or potassium PCA, and urea.

With respect to particle size, preferably the composition has at least 50% of the exfoliant particles with a particle size dimension along the major axis of the particle of from about 200 to 800 microns. Preferably about 50 to 80% by wt. of the exfoliant particles disintegrate to form smaller particles upon cleansing the skin. Preferably the exfoliating particles include agglomerated silica. More preferably at least 10% of the exfoliant particles have a color distinct from the composition which suspends the particles, and the exfoliant particles are present at a concentration level of less than about 10% by wt. preferably 5% of the composition. Most preferably, the exfoliant particles with a major axis greater than about 400 microns are at a concentration level of less than about 0.5% by wt.

Advantageously, the exfoliant particles are selected from polyethylene, microcrystalline wax, synthetic wax, jojoba esters, hydrogenated jojoba, amorphous silica, agglomerated silica, talc, tricalcium orthophosphate, or blends thereof, and the like.

Preferably the hydrophobic emollient is selected from fatty acids, triglyceride oils, mineral oil, petrolatum, lanolin alcohols, cholesterol, or blends thereof, and the like. More preferably a triglyceride oil is present. Most preferably the ratio of hydrophobic emollient to exfoliant is in the range of about 5:1 to 100:1.

Advantageously, the inventive composition includes about 0.1% to about 5% by wt. of the neat cleansing lotion of a lamellar stabilizing material consisting of a polymeric hydrophilic emulsifier modified at one or both ends with hydrophobic polyhydroxy fatty acid ester chain. Preferably the emulsifier has a polyalkylene glycol backbone chain of general formula: H(0(CH2)a) nOH wherein a is 2 to 4 and n is 2 to 60 having 1 to 50 C8 to C24 fatty acid group or groups attached to one or both sides of the backbone. Preferably the fatty acid group or groups attached to backbone chain is selected from hydroxystearic acid, palmitic acid, and blends thereof, and the like.

Advantageously, the pH of the inventive composition is in the range of about 5.0 to 7.5, preferably 5.5 to 6.5; and further includes less than about 5% by wt., preferably less than about 2% of soap.

In another aspect of the invention is a method for simultaneously exfoliating and moisturizing the skin comprising the steps of:
- a) providing a cleansing composition including
  - i) about 1 to 65% by wt., preferably 5 to 25 of one or more anionic surfactants;
  - ii) about 0.1 to 25% by wt., preferably 1 to 8 of one or more amphoteric surfactants;
  - iii) an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin;
  - iv) about 7 to 40%, preferably and 15–30%, by wt. of the total composition of a lipophilic emollient;
  - v) an effective amount of exfoliant particles for exfoliating the skin during cleansing wherein at least about 80% by wt. of the particles have a particle size dimension along the major axis of the particle of from about 100 microns to about 1000 microns.
- b) applying the composition to the skin;
- c) adding sufficient water to wet the skin and develop a lather; and
- d) rubbing the lather onto the skin for a time sufficient to remove dead skin cells and coat the underlying skin with the hydrophilic emollient.

The inventive liquid cleansing composition under actual use conditions is expected to show improvements in skin softness, skin smoothness, and similar consumer perceived benefits such as exfoliation efficiency, mildness, moisturization efficiency, deposition efficiency, cleansing efficiency, and a liquid cleansing composition property such as skin abrasiveness, etc. based on changes from the baseline for these measurements using liquid cleansing compositions without the inventive composition as quantified using the test methods described below. These skin benefit parameters can also be expressed quantitatively as the ratio of the inventive liquid cleansing composition response to the comparative liquid cleansing composition response. Where the magnitude of the inventive liquid cleansing composition benefit improvement is expected to exceed the numerical result of the comparative liquid cleansing composition, the observed ratio will be greater than 1.0; i.e. 1.02, 1.05, 1.07, 1.1, 1.2, 1.3, 1.4, 1.5, 1.6, 1.7, 1.8, 1.9, or 2.0. Where the magnitude of the inventive liquid cleansing composition benefit improvement is expected to fall below the numerical result of the comparative liquid cleansing composition, the observed ratio will be less than 1.0; i.e. 0.99, 0.98, 0.97, 0.95, 0.93, 0.90, 0.85, 0.80, 0.70, 0.60, 0.50, 0.40, 0.30, 0.20, or 0.10. Tables 1 to 4 below illustrate how various properties of the inventive liquid cleansing composition are expected to compare to four different comparative liquid cleansing compositions. The test methods that may be used to measure the properties are provided below.

TABLE 1

Inventive liquid cleansing composition vs. Comparative A[1]
(Competitor liquid cleansing composition with exfoliants)

| Property | Ratio vs. Comparative A |
|---|---|
| Mildness | >1 |
| Moisturization | >1 |
| Moisturizer deposition | >1 |
| Softness | >1 |
| Smoothness | >1 |
| Skin abrasiveness [2] | <1 |

[1]Comparative A: St Ives Apricot Body Scrub. Contains water, sodium laureth sulfate, acrylates copolymer, cocamidopropyl betaine, sodium hydroxide, *prunus armaenaca* (apricot) fruit extract, *helianthus annus* (sunflower) exract, *primula veris* extract, *sambucus nigra* flower extract, *chamomilla recutita* (matricaria) extract, propylene glycol, disodium edta, hydrogenated jojoba oil, polyethylene, panthenol, tocopheryl acetate, retinyl palmitate, ascorbic acid, dmdm hydantoin, fragrance, orange 4, red 33.
[2] Higher value means worse.

TABLE 2

Inventive liquid cleansing composition vs Comparative B[3]
(Syndet liquid cleansing composition without exfoliants)

| Property | Ratio vs. Comparative B |
|---|---|
| Exfoliation | >1 |
| Cleansing efficiency | >1 |
| Moisturizer deposition | =>1 |
| Softness | >1 |
| Smoothness | >1 |
| Liquid cleansing composition sensory exfoliation | >1 |

[3]Olay Complete Body wash, normal skin, contains: Water, Sodium Laureth Sulfate, Soybean Oil, Sodium Lauroamphoacetate, PEG-6 Caprylic/Capric Glyceride, Glycerin, Cocamide MEA, Palm Kernel Oil, Maleated Soybean Oil, Fragrance, Citric Acid, Magnesium Sulfate, Sodium Chloride, Sodium Citrate, Polyquaternium-10, Sodium Benzoate, DMDM Hydantoin, Disodium EDTA, Eucalyptus Oil, Patchouli Oil, Rosemary Oil

TABLE 3

Inventive liquid cleansing composition vs. Comparative C[4]
(Syndet liquid cleansing composition wherein comparitive formulation contains <10% total surfactants

| Property | Ratio vs. Comparative C |
|---|---|
| Mildness | >1 |
| Moisturizer deposition | =>1 |
| Softness | >1 |

TABLE 3-continued

Inventive liquid cleansing composition vs. Comparative C[4]
(Syndet liquid cleansing composition wherein comparitive formulation contains <10% total surfactants

| Property | Ratio vs. Comparative C |
|---|---|
| Smoothness | >1 |
| Skin abrasiveness [5] | <1 |
| Skin damage [6] | <1 |

[4]Olay Ohm exfoliating body scrub contains water, oxidized polyethylene, glyceryl stearate, TEA lauryl sulfate, coamide MEA, stearyl alcohol, fragrance, jasmine oil, rose flower oil, glycerin, TEA, acrylates, alkyl acrylate cross polymer, PEG-150 methacrylate, TiO2, methyl paraben, imidazoidinyl dioxide, urea, propyl parabens, disodium EDTA, bezophenone, iron oxide, Yellow 5
[5] Higher value means worse
[6] Higher value means worse Lamellar Compositions:

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consists of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 issued to Puvvada, et al., on Sep. 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase. Another way of measuring lamellar dispersions is using freeze fracture electron microscopy. Micrographs generally will show lamellar microstructure and close packed organization of the lamellar droplets (generally in size range of about 2 microns).

Isotropic Compositions

In contrast to lamellar surfactant solutions described above, single phase isotropic surfactant solutions are composed of completely miscible components whose microstructure does not vary with distance or direction in the solution. Upon comparison of the lamellar and isotropic compositions, it is found that isotropic structures do not deposit skin care ingredients in the same manner as lamellar structures.

Surfactants:

Surfactants are an essential component of the inventive liquid cleansing composition composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The anionic surfactant (which may comprise 3 to 40% by wt. of total composition) may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$–$C_{18}$ alkyl sulfate) or alkyl ether sulfate (including alkyl glyceryl ether sulfates), and the like. Among the alkyl ether sulfates are those having the formula:

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates, and the like.

Sulfosuccinates may be monoalkyl sulfosuccinates having the formula:

amido-MEA sulfosuccinates of the formula

wherein $R^4$ ranges from $C_8$–$C_{22}$ alkyl and M is a solubilizing cation;

amido-MIPA sulfosuccinates of formula

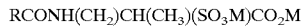

where M is as defined above.

Also included are the alkoxylated citrate sulfosuccinates; and alkoxylated sulfosuccinates such as the following:

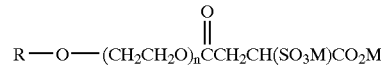

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

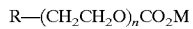

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic Acid" issued Feb. 28, 1995 to Ilardi et al., hereby incorporated by reference into the subject application. This compound has the general formula:

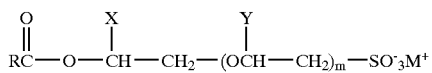

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Anionic surfactants are present in the inventive composition in the range of about 1 to 65% by weight, preferably about 5 to 25% by weight.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

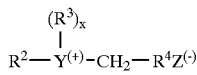

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

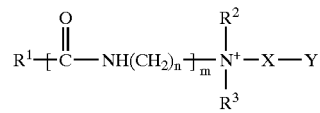

where $R^1$ is alkyl or alkenyl of 7 to 18 carbon atoms;
$R^2$ and $R^3$ are each independently alkyl hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$ Suitable amphoteric detergents within the above general formula include simple betaines of formula:

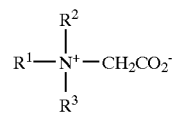

and amido betaines of formula:

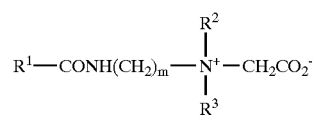

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

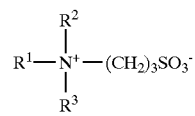

or

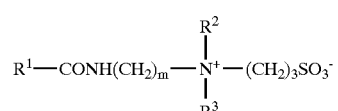

where m is 2 or 3, or variants of these in which $-(CH_2)_3SO^-_3$ is replaced by

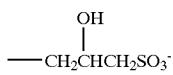

In these formulae $R^1$, $R^2$ and $R^3$ are as discussed previously.

Amphoacetates and diamphoacetates are also intended to be covered in possible zwitterionic and/or amphoteric compounds which may be used, especially C8–C20 amphoacetates or mixtures thereof, and the like. A suitable amphoacetate is sodium laurylamphoacetate.

The amphoteric/zwitterionic surfactant, when used, generally comprises 0.1%–25%, preferably 3 to 20% by weight, more preferably 1 to 8% of the composition.

A preferred surfactant system of the invention comprises the following: anionic surfactant (e.g. alkali metal alkyl ethersulfate), 2–50% by weight; amphoteric surfactant (e.g. alkyl betaine or alkyl amphoacetate), 3–20% by weight.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in U.S. Pat. No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula

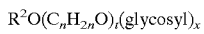

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic comprises 0 to 10% by wt. in the composition, preferably 0 to 5% by wt.

Lamellar Structurant

The compositions of the invention advantageously utilize lamellar structurants in an amount that is effective for forming a lamellar phase in the composition, preferably about 0.1% to 15% by wt., more preferably about 0.5 to 5% by wt. Such lamellar phase enables its composition to suspend particles more readily (e.g., emollient particles) while still maintaining good shear thinning properties. The lamellar phase also provides consumers with desired rheology ("heaping").

The structurant is selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin; and is preferably a fatty acid or ester derivative thereof, a fatty alcohol, or a hydroxystearin. More preferably the structurant is selected from the group consisting of lauric or isostearic acid, or trihydroxystearin.

Examples of fatty acids which may be used are $C_{10}$–$C_{22}$ acids such as the following: lauric acid, oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Oil/Emollient

One of the principle benefits of the invention is the ability to suspend oil/emollient particles in one or more lamellar phases in the multiphase composition. The following oil/emollients may optionally be suspended in the compositions of the invention.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil, sunflower seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of oil/emollients include mineral oil, petrolatum, silicone oil such as dimethyl polysiloxane, lauryl and myristyl lactate, fatty acid oils, triglycerides, glycerin, and the like.

As discussed above, the hydrophobic emollient is generally used in an amount from about 7 to 40%, preferably 15 to 30% by wt. of the phase in which it is found in. A portion of the hydrophobic emollient may be present in the form of solid or semi-solid beads. The beads are advantageously used in an amount from about 0 to 20%, preferably 0 to 10%, and more preferably 0 to 5% by wt.

In addition, the multiphase lamellar compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, TiO$_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides and the like as suds boosters.

Antioxidants such as, for example, butylated hydroxytoluene (BHT) may be used advantageously in amounts of about 0.01% or higher if appropriate.

Cationic conditioners which may be used include Polyquaternium-10, Quatrisoft LM-200, Polyquaternium-24, Merquat Plus 3330, Polyquaternium 39, Ucare polymer JR-400, and Jaguar® type conditioners.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sept. 15, 1992 to Montague, hereby incorporated by reference.

Ph and viscosity adjusters may be used such as citric acid, glycolic acid, lactic acid, other alpha or beta hydroxy acids, and the like.

Exfoliants

The inventive liquid cleansing composition contains exfoliant particles that help remove dry skin. Not being bound by theory, the degree of exfoliation depends on the size and morphology of the particles, and their hardness. Large, rough and hard particles are usually very harsh and irritating. Very small particles that are very soft may not serve as effective exfoliants. Hardness is typically measured using the Moh scale. The Moh's scale of hardness is the method used to measure the ability of one substance to scratch another. The scale ranges in order of increasing relative hardness from 1 (softest) to 10 (hardest).

Common exfoliants used in the art include Actinidia Chinensis (Kiwi) Seed, Alumina, Aluminum Iron Silicates, Aluminum Silicate, Amethyst Powder, *Amorphophallus Konjac* Root Powder, *Arachis Hypogaea* (Peanut) Flour, Attapulgite, *Avena Sativa* (Oat) Bran, *Avena Sativa* (Oat) Kernel Flour, *Avena Sativa* (Oat) Kernel Meal, *Bambusa Arundinacea* Stem Powder, Calcium Carbonate, Calcium Phosphate, Calcium Pyrophosphate, Calcium Sulfate, *Carya Illinoensis* (Pecan) Shell Powder, Chalk, Chitin, *Citrus Tangerina* (Tangerine) Peel, *Cocos Nucifera* (Coconut) Shell Powder, Colloidal Oatmeal, Conchiolin Powder, Coral Powder, *Corylus Avellana* (Hazel) Shell Powder, Diamond Powder, Diatomaceous Earth, Dicalcium Phosphate, Dicalcium Phosphate Dihydrate, Dolomite, Egg Shell Powder, Eijitsu, Elguea Clay, Emerald, *Fragaria Vesca* (Strawberry) Seed, Fuller's Earth, *Glycine Soja* (Soybean) Flour, *Helianthus Annuus* (Sunflower) Seed Meal, *Hordeum Distichon* (Barley) Seed Flour, *Hordeum Vulgare* Powder, *Hordeum Vulgare* Seed Flour, Hydrated Silica, Hydroxyapatite, Illite, *Juglans Mandshurica* (Walnut) Shell Powder, *Juglans Regia* (Walnut) Shell Powder, Kaolin, *Kurumi Kaku*, Lauryl Acrylate/VA Crosspolymer, *Lithothamnium Calcarum* Powder, *Lithothamnium Corallioides* Powder, Loess, *Luffa Cylindrica* Fruit, Magnesium Potassium Fluorosilicate, Magnesium Sodium Fluorosilicate, Magnesium Trisilicate, *Melaleuca Alternifolia* Leaf Powder, Microcrystalline Cellulose, Montmorillonite, Moroccan Lava Clay, Mother of Pearl, Myristyl Betaine, *Oenothera Biennis* (Evening Primrose) Seed, *Olea Europaea* (Olive) Fruit, *Olea Europaea* (Olive) Husk Powder, *Olea Europaea* (Olive) Seed Powder, *Oryza Sativa* (Rice) Bran, *Oryza Sativa* (Rice) Germ Powder, Oubaku, Oyster Shell Powder, *Papaver Somniferum* Seed, Perlite, *Persea Gratissima* (Avocado) Fruit Powder, *Phaseolus Radiatus* Seed Starch, Platinum Powder, Polyethylene, Potassium Undecylenoyl Glutamate, *Prunus Amygdalus Dulcis* (Sweet Almond) Seed Meal, *Prunus Amygdalus Dulcis* (Sweet Almond) Shell Powder, *Prunus Armeniaca* (Apricot) Seed Powder, *Prunus Mume* Fruit, *Prunus Persica* (Peach) Seed Powder, Pumice, Quartz, *Rubus Idaeus* (Raspberry) Seed, Salt Mine Mud, Sand, Sea-Salt, *Secale Cereale* (Rye) Seed Flour, Silica, Sodium Bicarbonate, Sodium Hydroxypropyl Starch Phosphate, Sodium Magnesium Fluorosilicate, Sodium Silicoaluminate, *Symphytum Officinale* Leaf Powder, Talc, *Theobroma Cacao* (Cocoa) Shell Powder, Tin Oxide, Titanium Oxynitride, Topaz, Touki, Tricalcium Phosphate, *Triticum Vulgare* (Wheat) Bran, *Triticum Vulgare* (Wheat) Germ Powder, *Triticum Vulgare* (Wheat) Kernel Flour, *Triticum Vulgare* (Wheat) Starch, *Vaccinium Angustifolium* (Blueberry) Seed, *Vaccinium Macrocarpon* (Cranberry) Seed, Volcanic Ash, Wood Powder, Yokuinin, *Zea Mays* (Corn) Cob Meal, *Zea Mays* (Corn) Cob Powder, *Zea Mays* (Corn) Kernel Meal, *Zea Mays* (Corn) Seed Flour, *Zea Mays* (Corn) Starch, and Zirconium Silicate. These exfoliants come in a variety of particle sizes and morphology ranging from micron sized to a few mm. They also have a range of hardness. Some examples are given in table 5 below.

TABLE 5

| Material | Hardness (Mohs) |
| --- | --- |
| Talc | 1 |
| Calcite | 3 |
| Pumice | 4–6 |
| Walnut Shells | 3–4 |
| Dolomite | 4 |
| Polyethylene | ~1 |

The exfoliants in the present invention have particle sizes where at least 25% by weight of the particles (preferably at least 50%) have a major axis (i.e. the longest dimension of an irregular particle or the diameter of a spherical particle) in the range of about 100 to 1000 microns; preferably about 200 to 600 microns, and most preferably where the smallest particle in this weight fraction has its major axis greater than 150 microns; and wherein the exfoliant particle has a hardness sufficient that a significant percentage of the particles will disintegrate into smaller particles during cleansing. Preferably about 50 to 80% of the particles disintegrate during cleansing.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

TABLE 6

Examples of inventive compositions.

| Ingredients | weight percent | | |
|---|---|---|---|
| | Example 1 | Example 2 | Example 3 |
| sunflower seed oil | 16.00 | 16.00 | 21.30 |
| silica particles | 2.00 | 2.00 | 1.00 |
| PE beads | 0.00 | 0.00 | 0.75 |
| synthetic wax beads | 0.50 | 0.00 | 0.00 |
| jojoba beads | 0.00 | 1.00 | 0.00 |
| sodium laureth sulfate | 12.30 | 0.00 | 12.30 |
| ammonium lauryl sulfate | 0.00 | 4.00 | 0.00 |
| ammonium laureth sulfate | 0.00 | 4.00 | 0.00 |
| cocamidopropyl betaine | 5.70 | 4.00 | 0.00 |
| sodium lauroamphoacetate | 0.00 | 0.00 | 5.00 |
| lauric acid | 2.90 | 2.90 | 0.00 |
| isostearic acid | 0.00 | 0.00 | 2.90 |
| PEG-30 dipolyhydroxystearate | 0.25 | 0.25 | 0.25 |
| guar hydroxypropyltrimonium chloride | 0.70 | 0.70 | 0.70 |
| Petrolatum | 3.70 | 3.70 | 3.70 |
| glycerin | 5.70 | 5.70 | 5.70 |
| preservatives, minors | 1.00 | 1.00 | 1.00 |
| TiO2 | 0.05 | 0.05 | 0.05 |
| water | q.s. 100 | q.s. 100 | q.s. 100 |

Note:
Minors include fragrance, salts, preservatives, dyes and/or pigments, etc.

Description of Test Methods

Methods of Testing

One or more of the following tests can be used to characterize the inventive liquid cleansing composition and compare it to comparative liquid cleansing compositions.

a) Exfoliation Test:

A suitable corneocyte staining dye (eg: gentian violet) is applied to a 2–5 cm diameter spot on skin (arm/leg or any other part of the body as desired) and left on for 5 minutes to ensure uniform staining of the skin surface cells (corneocytes). The excess dye is then washed away by rinsing the spot under running water at 35 C for 30 secs with no rubbing of the skin.

The stained sites are then washed with the test product. For the liquid cleansing composition the following wash method is adopted. Wet the spot on skin, pre-wet the liquid cleansing composition, rub liquid cleansing composition directly on spot for 30 secs (back and forth motion), rinse for 15 secs under running water at 35 C for 30 secs with no rubbing of the skin and gently pat dry. Allow the site to dry for 10 minutes. A d-squame tape (Cuderm® manufactured by CuDerm Corporation, (Dallas, Tex.) is applied on the washed spot under a uniform pressure for 30 secs and then removed. The d-squame tape is imaged using a Kodak DCS 420 digital camera with a 105 mm lens. The image is analyzed using Optimas image analysis software for area covered/total intensity of stained cells (Optimas® is available from Media Cybernetics, Silver Springs, Md.). By comparing this data to similar information from an unwashed site, one can estimate the amount of exfoliation caused by the test product as follows:

Exfoliation=(area of d-squame covered by stain on unwashed site−area of d-squame covered by stain on washed site)/(area of d-squame covered by stain on unwashed site)

Alternately exfoliation can also be evaluated in a consumer test as follows:

The Test Protocol Consists of

1) Recruiting aprox. 10–20 women in the age group of 25–65 and who are complexion liquid cleansing composition users.

2) Use test and comparative products for a week each. Half the panelists would use the test product first and the other half would use the comparative product first.

3) At the end of the test, the panelists rate their preference (on a 0–5 point scale) on the attribute of "exfoliation".

The degree of exfoliation is defined as the consumer rating on the 0–5 point scale b) Mildness Test:

i) Forearm Controlled Application Test (FCAT) Clinical Test Methodology

This controlled washing test is similar to that described by Ertel et al (A forearm controlled application technique for estimating the relative mildness of personal cleansing products, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores >1.0 and erythema scores >0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Liquid Cleansing Composition Products

1. Both arms are washed simultaneously. Test sites are treated in a sequential manner starting with the site closest to the flex area, ending with the site proximal to the wrist.

2. The sites closest to the flex area of the inner forearm of both the right and left arm are moistened with warm water (90°–100° F.).

3. A moistened Masslinn towel is rubbed in a circular motion on a wetted test liquid cleansing composition for approximately 6 seconds by study personnel which will result in 0.2–0.5 g of product to be dispensed.

4. The site is washed with the designated product for 10 seconds followed by a 90-second lather retention phase.

5. The above procedure (1–4) is then repeated for each of the test sites. Sites are then be rinsed (e.g. using a temperature of 35 C) for fifteen seconds and patted dry.

6. Upon completion the entire procedure is repeated (two washes/session).

For Liquid Products: A technician will prepare liquid products just prior to the wash session by dispensing between 0.1 g and 0.5 g of product either directly onto the skin or a moistened Maslinn towel or alternative application material. The washing procedure outlined above will then be used.

Evaluation Methods

Baseline visual assessments are made prior to the start of the product application phase, and immediately before each wash session thereafter, to evaluate dryness and erythema The final visual evaluation is conducted on the afternoon of the final day.

The 0–6 grading scale shown in Table 8 is used to assess the test sites for dryness and erythema. To maintain the evaluator's blindness to product assignment, visual assessments are conducted in a separate area away from the product application area.

TABLE 8

Eythema and Dryness grading scale.

| Grade | Erythema | Dryness |
|---|---|---|
| 0 | None | None |
| 1.0 | Liquid cleansing compositionely perceptible | Patches of slight powderiness and redness occasional patches of small scales may be seen. Distribution generalized. |
| 2.0 | Slight redness | Generalized slight powderiness. Early cracking or occasional small lifting scales may be present |
| 3.0 | Moderate redness | Generalized moderate powderiness and/or heavy cracking and lifting scales. |
| 4.0 | Heavy or substantial | Generalized heavy powderiness and/or redness heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study.

Mildness of test product is calculated as 1/(mean change in dryness at end of the study)

In addition to visual evaluation, instrumental assessments of the treated sites will be conducted using an evaporimeter and skin conductance meter as described in the reference above.

ii) Patch Testing 48 hr continuous or 14 day cumulative insult patch test: In the 48 hr patch test 5–15% solution/slurry of the product is applied onto the upper arm/back of the subject using a standard cotton pad. Irritation response is recorded for up to 24 hrs after removal of the patch. In the 14 day cumulative test a 5–15% solution/slurry of the product is applied repeatedly every 24 hrs for 14 days. Irritation response is recorded for up to 24 hrs after removal of patch.

Mildness of test product is evaluated as 1/(mean erythema at 24 hr after final patch removal).

c. Moisturization Test:

i) Single Application Moisturization Test:

Each outer, lower leg of a test subject will be divided into three sites, 2.5 by 2.5 inch squares (upper, middle and lower) for a total of 6 test sites per subject. One or two of the sites will be untreated and will be included in the randomization of products. A technician will treat the sites once or twice with the designated amount of test material for 10 seconds. Cleansing products will remain on the test sites for a maximum of 90 seconds. Sites will be rinsed for 30 seconds each (e.g. using a temperature of 35 C), ensuring that the test material from one site does not contaminate another site. After rinsing, the test sites are gently dried with a paper towel. The application consists of dosing with up to 5 different test materials on the designated sites, one material per test site, and one or two untreated sites.

Test Phase: Visual Evaluation

The scale as shown in Table 9 will be used to assess the test sites for dryness.

TABLE 9

| Grade | Dryness Scale | Erythema Scale |
|---|---|---|
| 0.0 | No dryness | No erythema |
| 0.5 | Perceptible dryness, fine white lines | |
| 1.0 | Fine dry lines, white powdery look and/or some uplifting flakes, on less than 30% of the test site | Mild erythema |
| 1.5 | More uniform flaking, covering 30–50% of the test site | |
| 2.0 | Uniform, marked flaking covering more than 50% of the test site area and/or isolated scaling | Moderate confluent erythema |
| 2.5 | Slight to moderate scaling | |
| 3.0 | Moderate to severe scaling with some uplifting of the scales | Marked erythema |
| 3.5 | Severe scaling and/or slight fissuring | |
| 4.0 | Severe scaling and severe fissuring | Deep erythema |

Baseline visual assessments will be made prior to the start of the product application phase and thereafter, immediately before each of the instrumental assessments, to evaluate skin dryness and erythema. One trained evaluator will conduct all visual evaluations during the product application phase. The evaluator will examine both lower legs with the aid of an illuminated magnifying lamp with a 3 diopter lens and a shadow-free circular cool white fluorescent light source.

Instrumental Assessment

All instrumental evaluations will be taken following a 30-minute acclimation period. The indoor humidity and temperature data will be recorded and included in the final report. Instrumental measurements may be taken at some or all of the following time points: 0, 1, 2, 4, 6, 8 and 24 hours after product application. Instruments to be used with this protocol include: ServoMed Evaporimeter with EP1 or EP2 probe, Corneometer CM820, the Skicon Skin Hygrometer with the MT-8C probe, and the Moisture Checker. The room temperature will be maintained at 68° to 77° F. and 30% to 40% Relative Humidity.

Moisturization is defined as mean change from baseline of (visual dryness or skin hydration) at a given point in time/ ii) Multiple Application Moisturization Test:

Alternately the moisturization test can be conducted via multiple application of the product over a period of 5 days. Product applications are made twice everyday approximately 3 hrs apart. The wash procedures are similar to the single application test, but evaluations are made at baseline, before every wash and 3 hrs after the final wash on D5.

d) Moisturizer Deposition Test:

Precondition the subject's skin (arms/legs) with non-moisturizer containing product for up to 2 days prior to testing. A baseline extraction is performed to estimate level of moisturizer (eg: fatty acids) present on the skin prior to product application. Controlled single application of product to skin (arms or legs) is made. For wash, liquid cleansing composition is rubbed on skin for 30 secs and the lather left on for 90 secs, rinsed for 30 secs (e.g. using a temperature of 35 C) then gently pat dry. Following this, the site is extracted using a suitable solvent (IPA)/methanol 1:1). The extraction is performed as follows: A glass cup (3 cm diameter) is placed on the skin. 3 mls of solvent is placed into this and gently stirred with a glass rod for 2 minutes. The solvent is removed with a pipette. This step is repeated with a fresh 3 mls of solvent, to collect a total of 6 mls extract. The extracts are analyzed for stearic acid/palmitic acid content using either LC/MS or GC/MS, or the like.

Alternately sample collection can be performed using a tape stripping procedure. For this, a suitable tape (eg: white sellotape) is placed on skin under controlled presssure for 2 minutes and gently removed. Typically 2 sequential tape strips are collected from each sampling site. The tapes are analyzed via LC/MS or GC/MS, or the like.

e) Skin Abrasiveness Test

Skin abrasiveness is defined as consumer rated response of abrasivity on a 0–9 scale (0 means no abrasion, 10 is abrasivity caused by a pouf (i.e. a showering implement composed of thin plastic filaments, see also e.g. U.S. Pat. No. 5,650,384 to Gordon et al.).

This test is performed with 50 untrained consumers. They are asked to rate the abrasiveness of the test product on a 0–9 point scale. The data is normalized based on their response to a liquid cleansing composition with no exfoliants which is assigned a value of zero and a pouf that is assigned a value of 9. The test products are applied to the flex area of the forearm by wetting the liquid cleansing composition and rubbing back and forth 10–15 times.

f) Skin Damage Test

Skin damage is determined using cross polarized skin imaging as described below.

A baseline cross polarized image of the subject's forearm is obtained using for example a hand held cross polarized imaging device (Charm View, Moritex Corporation, San Diego, Calif.). Alternately a stereomicroscope with polarizer accessories can be used to achieve the same result. The forearm of subject's skin is washed with the product using the following protocol. 0.5 ml of the product is dispensed on to skin (prewet) and rubbed back and forth about 20 times. The wash can be repeated up to 3 times everyday for up to 3 days. An image is obtained of the test site 5 minutes after every wash and prior to each wash.

Images are analyzed using Optimas/Image Pro software (r) to determine a) degree of whiteness (lines/scratches/scaling) and b) degree of redness on skin.

Skin damage is defined as % increase in whiteness and/or redness in the image after wash.

g) Cleansing Efficacy Test

Model dirt (sebum/makeup—e.g. lipstick or mascara) is applied to a designated area on the forearm/face. The site is washed with the product. For wash, the liquid cleansing composition is rubbed on skin for 1 minute, rinsed for 30 secs (e.g. using a temperature of 35 C), and gently pat dry. Amount of soil/makeup removed is estimated from the difference in the chromammeter readings using e.g. a Minolta Chromameter®, Model CM 2002 taken before and after wash. Alternately, high magnification digital mages are collected and analyzed using Optimas® software to quantitate the amount of soil/makeup removed during the wash.

Make Up Application:

Makeup will be applied to the 3.5×2.5 cm marked area on the inner side of the forearms in the manner consistent with its normal use. Cosmetic products are to be applied in a standardized way to ensure that approximately equal weights of make-up are transferred and that coverage of the test area is uniform. The application standards for the makeups are:

1.) Liquid make-up—20 μl pipette to the site and spread uniformly with gloved index finger.
2.) Lipstick—Three overlapping swipes.
3.) Eye Color Stick—Three overlapping swipes.
4.) Mascara—spread uniformly using spatula for even coverage.

Soil Application:

Soils will be applied to the 3.5×2.5 cm marked area on the inner side of the forearms in the manner described below and is specific to each individual study if soils are being used. The application techniques for the soils are:

1.) Grease—0.25 g–1.5 g. will be applied.
2.) Food—0.25 g–1.5 g. will be applied.
3.) Protein—0.25 g–1.5 g. will be applied.

Product Testing:

Baseline measurements will be performed using the Minolta Chromameter CM-2002. Make-up or Soil will then be applied to the delineated test sites as described above. Chromameter measurements will be taken again after the make up has dried for 10 minutes, then the make-up/soil will be removed. The standard washing procedure used to remove the make-up/soil is a 30-second wash with 0.5 cc of a liquid product with a 15-second rinse under running water using a suitable constant temperature (e.g. 35 C). When a towelette product is being used, the towelette is rubbed over the test site in a circular motion for 15 seconds. Final Chromameter measurement will be taken after the make-up/soil has been removed. This procedure may be performed twice a day for a period of up to 3 days. In repeat application studies visual assessments will be made for dryness and erythema using the standard visual grading scale as described above.

h) Skin Smoothness

Skin smoothness is evaluated (clinically) via Primos® (in-vivo optical skin topography measuring device supplied by GFM Esstezhnik GmbH, Berlin, Germany). Baseline roughness is measured (on leg/arms—starting dryness around grade 1–2). For wash, liquid cleansing composition rubbed on skin for 30 secs and the lather left on for 90 secs, rinsed for 30 secs at 35 C. Measure again the roughness 30 minutes after wash process. This procedure may be performed twice a day for a period of up to 5 days.

Smoothness is defined as the mean decrease in roughness at end of study period. Alternately skin smoothness can also be evaluated in a consumer test as follows:

The consumer test protocol consists of:

1) Recruiting aprox. 10–20 women in the age group of 25–65 and who are complexion liquid cleansing composition users.

2) Use test and comparative products for a week each. Half the panelists would use the test product first and the other half would use the comparative product first.

1) At the end of the test, the panelists rate their preference (on a 0–5 point scale) on the attribute of "Skin feels smoother".

Smoothness is defined as the consumer rating on the 0–5 point scale i) Skin Softness Skin softness may be evaluated using the Linear Skin Rheometer (Goodyear Scientific Instruments, UK). Exfoliated skin has less dry flakes—hence is more soft/less stiff. The test involves baseline skin rheometer readings (on the leg/arms) to measure the dynamic spring constant (mgf/mm) of skin which is related to skin stiffness/softness. For wash, the liquid cleansing composition is rubbed on the skin for 30 secs and the lather left on for 90 secs, rinsed for 30 secs (at a suitable temperature e.g. 35 C), and the skin is gently pat dry. Next measure skin stiffness/softness 30 minutes after wash. This procedure may be performed twice a day for a period of up to 5 days. Softness is defined as the mean decrease in dynamic spring constant during the study period observed during the study period.

Alternately skin softness can also be evaluated in a consumer test as follows:

The Test Protocol Consists of

1) Recruiting approx. 10–20 women in the age group of 25–65 and who are complexion liquid cleansing composition users.

2) Use test and comparative products for a week each. Half the panelists would use the test product first and the other half would use the comparative product first.
3) At the end of the test, the panelists rate their preference (on a 0–5 point scale) on the attribute of "Skin feels softer".

Softness is defined as the consumer rating on the 0–5 point scale i) pH Test Method Form an aqueous slurry by blending 10 grams of the liquid cleansing composition formula with 90 g of water to create a 10% slurry. The pH of the slurry is then measured at 25 C.

j) Liquid Cleansing Composition Sensory Exfoliation Index

The liquid cleansing composition sensory exfoliation index is determined using the following procedure: The user takes the liquid cleansing composition in one hand and rotates it under running water at 35 C. The number of rotations required for the exfoliant to be perceived (i.e. by tactile sensation) by the user is recorded. The liquid cleansing composition exfoliation index is defined as the mean number of rotations required to perceive the exfoliant particles in the liquid cleansing composition.

i) General Consumer Test Protocol

The Test Protocol Consists of

1) Recruiting aprox. 10–20 women in the age group of 25–65 and who are complexion liquid cleansing composition users.

2) Use test and comparative products for a week each. Half the panelists would use the test product first and the other half would use the comparative product first.

2) At the end of the test, the panelists rate their preference on a 0–5 point scale for the following attributes:

Exfoliates

Provides Gentle Exfoliation

Mositurizes and exfoliates

Skin feels softer

Skin feels smoother

Is good for dry skin

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A lamellar liquid cleansing composition, comprising:
   a. about 1 to 65% by wt. of one or more anionic surfactants;
   b. about 0.1 to 25% by wt. of one or more amphoteric surfactants;
   c. at least about 10% by wt. of total surfactants including one or more of anionic, amphoteric, nonionic surfactants, or a blend thereof;
   d. an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin;
   e. about 7 to about 40% by wt. of the total composition of a lipophilic emollient; and
   f. an effective amount of exfoliant particles for exfoliating the skin during cleansing wherein at least about 80% by wt. of the particles have a particle size dimension along the major axis of the particle of from about 100 microns to about 1000 microns wherein said exfoliant particles are selected from polyethylene, microcrystalline wax, synthetic wax, jojoba esters, hydrogenated jojoba, amorphous silica, agglomerated silica, talc, tricalcium orthophosphate, or blends thereof.

2. The composition of claim 1 wherein at least 50% of surface dead skin cells according to the d-squame comparison test and simultaneously will provide a minimum deposition of about 5 micrograms per square centimeter of a lipophilic emollient.

3. The composition of claim 1 wherein the ratio of total anionic surfactants to total amphoteric surfactants is in the range of about 5 to 1.

4. The composition of claim 1 wherein said composition provides measurable exfoliation according to the d-squame test comparison without inducing skin damage of more than about a 10% change in degree of skin whiteness or more than about a 10% change in degree of skin redness as determined by a cross polarized skin imaging test comparison after 3 washing applications per day for one day.

5. The composition of claim 1 wherein the cleansing composition further comprises about 1 to 10% by wt. of the total composition of humectants.

6. The composition of claim 1 wherein at least 50% of the exfoliant particles have a particle size dimension along the major axis of the particle of from about 200 to 800 microns.

7. The composition of claim 1 wherein about 50 to 80% by wt. of the exfoliant particles disintegrate to form smaller particles upon cleansing the skin, Preferably the exfoliating particles include agglomerated silica.

8. The composition of claim 1 wherein at least 10% of the exfoliant particles have a color distinct from the composition which suspends the particles.

9. The composition of claim 1 wherein the exfoliant particles are present at a concentration level of less than about 10% by wt. of the composition.

10. The composition of claim 1 wherein the exfoliant particles greater than about 400 microns are at a concentration level of less than about 0.5% by wt.

11. The composition of claim 1 wherein the hydrophobic emollient is selected from fatty acids, triglyceride oils, mineral oil, petrolatum, lanolin alcohols, cholesterol, or blends thereof.

12. The composition of claim 1 wherein the ratio of hydrophobic emollient to exfoliant is in the range of about 5:1 to 100:1.

13. The composition of claim 1, further comprising:
about 0.1% to about 5% by wt. of the neat cleansing lotion of a lamellar stabilizing material consisting of a polymeric hydrophilic emulsifier modified at one or both ends with hydrophobic polyhydroxy fatty acid ester chain.

14. The composition of claim 13 wherein the emulsifier has a polyalkylene glycol backbone chain of general formula:

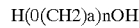

wherein a is 2 to 4 and n is 2 to 60 having 1 to 50 C8 to C24 fatty acid group or groups attached to one or both sides of the backbone.

15. The composition of claim 13 wherein the fatty acid group or groups attached to backbone chain is selected from hydroxystearic acid, palmitic acid, and blends thereof.

16. The composition of claim 1 wherein the pH is in the range of about 5.0 to 7.5.

17. The composition of claim 1 further comprising less than about 5% by wt. of soap.

18. A method for simultaneously exfoliating and moisturizing the skin comprising the steps of:
 a) providing a cleansing composition including
  i) about 1 to 65% by wt. of one or more anionic surfactants;
  ii) about 0.1 to 25% by wt. of one or more amphoteric surfactants;
  iii) at least about 10% by wt. of total surfactants including one or more of anionic, amphoteric, nonionic surfactants, or a blend thereof;
  iv) an effective amount of a lamellar phase inducing structurant for forming a lamellar phase in the cleansing composition, the structurant being selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and hydroxystearin;
  v) about 7 to 40% by wt. of the total composition of a lipophilic emollient;
  vi) an effective amount of exfoliant particles for exfoliating the skin during cleansing wherein at least about 80% by wt. of the particles have a particle size dimension along the major axis of the particle of from about 100 microns to about 1000 microns wherein said exfoliant particles are selected from polyethylene, microcrystalline wax, synthetic wax, jojoba esters, hydrogenated jojoba, amorphous silica, agglomerated silica, talc, tricalcium orthophosphate, or blends thereof;
 b) applying the composition to the skin;
 c) adding sufficient water to wet the skin and develop a lather;
 d) rubbing the lather onto the skin for a time sufficient to remove dead skin cells and coat the underlying skin with the hydrophilic emollient.

* * * * *